(12) United States Patent
Earle et al.

(10) Patent No.: US 7,084,317 B2
(45) Date of Patent: Aug. 1, 2006

(54) OXIDATIVE HALOGENATION OF AROMATIC COMPOUND

(75) Inventors: Martyn John Earle, Belfast (GB); Suhas Prabhakar Katdare, Belfast (GB)

(73) Assignee: The Queen's University of Belfast, Belfast (GB)

(*) Notice: Subject to any disclaimer, the term of this patent is extended or adjusted under 35 U.S.C. 154(b) by 156 days.

(21) Appl. No.: 10/398,670

(22) PCT Filed: Oct. 5, 2001

(86) PCT No.: PCT/GB01/04424

§ 371 (c)(1), (2), (4) Date: Jun. 16, 2003

(87) PCT Pub. No.: WO02/30852

PCT Pub. Date: Apr. 18, 2002

(65) Prior Publication Data

US 2004/0034260 A1    Feb. 19, 2004

(30) Foreign Application Priority Data

Oct. 10, 2000   (GB) ................. 0024752.8

(51) Int. Cl.
*C07C 17/00* (2006.01)

(52) U.S. Cl. ............... 570/190; 570/203; 570/206; 570/207; 570/208; 570/210

(58) Field of Classification Search ............. 570/190, 570/203, 206, 207, 208, 210
See application file for complete search history.

(56) References Cited

U.S. PATENT DOCUMENTS 4,075,252 A    2/1978    Boudakian ............... 260/649

FOREIGN PATENT DOCUMENTS

| GB | 1159950 A | | 7/1969 |
| SU | 1077874 A | | 3/1984 |
| WO | WO 89/08630 | * | 9/1989 |
| WO | WO 00 37400 A | | 6/2000 |

OTHER PUBLICATIONS

Boon et al., "Catalysis and Reactivity of Electrophilic Reactions in Room Temperature Choroaluminate Molten Salts", *J. Electrochem. Soc.* 134:C510 (1987).

* cited by examiner

*Primary Examiner*—Sikarl A. Witherspoon
(74) *Attorney, Agent, or Firm*—Drinker Biddle & Reath LLP; Daniel A. Monaco

(57) ABSTRACT

A process for the halogenation of an aromatic compound wherein the aromatic compound is admixed with a halogenating agent in the presence of an ionic liquid is described. The method in preferably halide, sulfur or nitrate ionic liquids has significant advantages over conventional halogenation reactions. These are that the reaction starts with, e.g., a halide salt rather than, e.g., a halogen, and is therefore more convenient and safer. Also, when the reaction is performed in a nitrate ionic liquid, the only by-product is water.

14 Claims, No Drawings

OXIDATIVE HALOGENATION OF AROMATIC COMPOUND

The present invention relates to a process for halogenation of aromatic compounds.

The halogenation of aromatic compounds can be achieved by a number of classical methods. This involves the reaction of an aromatic compound with a halogen[1] in the presence of a Lewis acid[1]. Other methods include use of hypohalous acid,[2] N-chloro[3] and N-bromo amides,[3], dibromoisocyanuric acid in $H_2SO_4$,[4] $Cl_2O$ in $H_2SO_4$,[5] and metal halides such as iron(III) chloride.[6] In the early 1960s it was found that the interaction of a halide salt with nitric acid resulted in oxidative halogenation,[7] where $HNO_3$ oxidised a halide ion prior to the reaction with an aromatic compound.[8] The reduced nitrous acid formed is unstable and is oxidised back to nitric acid by air.[9]

According to one aspect of the present invention, there is provided a process for the halogenation of an aromatic compound wherein the aromatic compound is admixed with a halogenating agent in the presence of an ionic liquid.

The method for the halogenation of aromatic compounds in preferably halide, sulfur or nitrate ionic liquids has significant advantages over conventional halogenation reactions. These are that the reaction starts with e.g. a halide salt rather than e.g. the halogen, and is therefore more convenient and safer. Also, when the reaction is performed in a nitrate ionic liquid, the only by-product is water.

The ionic liquid can act as a catalyst for the reaction and can re recycled and reused. This is outlined in Scheme 1.

Scheme 1
The oxidative halogenation of aromatic compounds in ionic liquids.

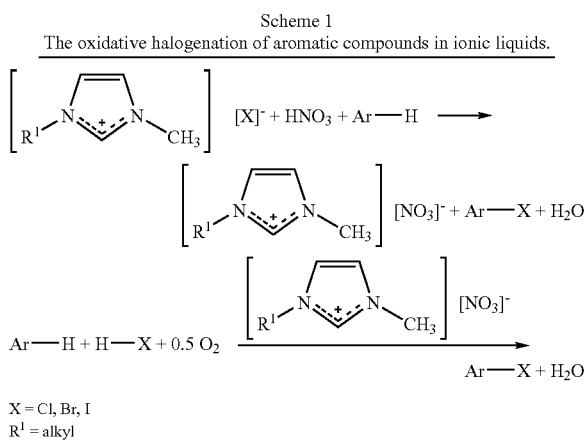

X = Cl, Br, I
$R^1$ = alkyl

Ionic liquids consist of two components, which are a positively charged cation and a negatively charged anion. Generally, any compound that meets the criteria of being a salt (consisting of an anion and cation) and is fluid at or near the reaction temperature or exists in a fluid state during any stage of the reaction may be defined as an ionic liquid.

The cation for the present process is preferably a 1-alkylpyridinium cation such as 1-hexylpyridinium. Other cations for this process are alkyl- or poly-alkylpyridium, phosphonium, alkyl- or polyalkylphosphonium, imidazolium, alkyl- or polyalkylimidazolium, ammonium, alkyl- or polyalkylammonium, alkyl- or polyalkylpyrrazolium, alkyloxonium or alkylsulfonium cations.

The anion for the present process is preferably a halide (chloride, bromide or iodide) or a nitrate. Other halide or nitrogen containing anions are also suitable. Other anions include alkylsulfate, such as methanesulfonate, trifluoromethanesulfonate, and hydrogensulfate. Non sulfur-containing anions include those based on nitrogen, phosphorus, boron, silicon, selenium, tellurium, halogens, oxoanions of metals, and antimony, and bismuth based.

More than one ionic liquid or any combination of ionic liquids may be used.

| Suitable Process Conditions | |
|---|---|
| Temperature | ideally 20–80° C. but to include −40° C. to 200° C. |
| Pressure: | ideally, atmospheric, but include 1 mbar to 100 bar |
| Time: | ideally 1 to 48 hours, can be 1 minute to 1 month. |

Room temperature ionic liquids have been used to great effect as solvents for a number of reactions,[10] for example Friedel-Crafts reactions,[11] isomerisations of fatty acid derivatives,[12] dimerisation reactions of alkenes,[13] Diels-Alder reactions[14] and hydrogenation reactions.[15]

Room temperature ionic liquids such as [emim]Cl—$AlCl_3$ (X=0.67) ([emim]$^+$=1-methyl-3-ethylimidazolium cation), have been found to been used for many reactions,[16] although chloroaluminate(III) are moisture sensitive.

Preferably, the present invention uses water stable ionic liquids as media for the reaction.

The halogenation reactions of aromatic compounds using concentrated nitrating agent, e.g. nitric acid in combination with a halide salt (ionic liquid) were found to be successful. In addition, the reaction of hydrohalic acid with an aromatic compound in a nitrate ionic liquid was found to halogenate aromatic compounds in a similar manner. The results of the halogenation of benzene, toluene, naphthalene and anisole by the reaction of a halide ionic liquid (molten salt) and nitric acid are shown in Table 1.

TABLE 1

The nitration of aromatic compounds with $HNO_3$, in ionic liquids.

| Aromatic Compound | Ionic Liquid | Eq. 68% $HNO_3$ | Temp/ ° C. | Time/ h. | Product(s) | % Yield |
|---|---|---|---|---|---|---|
| Benzene | [$C_{10}$mim] Cl | 3 | 80 | 120 | $C_6H_5$—Cl | 99 |
| Toluene | [$C_{10}$mim] Cl | 2.5 | 110 | 120 | 2—Cl—$C_6H_4$—$CH_3$ | 62 |
|  |  |  |  |  | 4—Cl—$C_6H_4$—$CH_3$ | 37 |
| Toluene | [$C_{12}$mim] Br | 3 | 110 | 72 | 2—Br—$C_6H_4$—$CH_3$ | 39 |
|  |  |  |  |  | 4—Br—$C_6H_4$—$CH_3$ | 60 |
| Anisole | [$C_{10}$mim] Cl | 3.3 | 20 | 72 | 2—Cl—$C_6H_4$—$OCH_3$ | 20 |
|  |  |  |  |  | 4—Cl—$C_6H_4$—$OCH_3$ | 79 |
| Anisole | [$C_{12}$mim] Br | 2 | 50 | 1 | 4—Br—$C_6H_4$—$OCH_3$ | 99 |

TABLE 1-continued

The nitration of aromatic compounds with HNO₃, in ionic liquids.

| Aromatic Compound | Ionic Liquid | Eq. 68% HNO₃ | Temp/ °C. | Time/ h. | Product(s) | % Yield |
|---|---|---|---|---|---|---|
| Anisole | [Bu₄N] I | 3 | 100 | 24 | 4—I—C₆H₄—OCH₃ | 97 |
| Naphthalene | [C₁₂mim] Br | 2 | 50 | 2 | 1—Br—C₁₀H₇ | 98 |

In Table 1, [C$_{10}$mim] is an abbreviation used to represent the [1-decyl-3-methylimidazolium] ion and [C$_{12}$mim] is an abbreviation used to represent the [1-dodecyl-3-methylimidazolium] ion.

The results of the halogenation of toluene and anisole by the reaction of a hydrohalic acid and nitrate ionic liquid as shown in Table 2.

TABLE 2

The nitration of aromatic compounds with 1-butyl-3-methylimidazolium nitrate, in ionic liquids.

| Aromatic Compound | Acid | Temp./° C. | Time/h. | Product(s) | % Yield |
|---|---|---|---|---|---|
| Toluene | 38% HCl | 100 | 96 | 2—Cl—C₆H₄—CH₃ | 60 |
|  |  |  |  | 4—Cl—C₆H₄—CH₃ | 39 |
| Toluene | 49% HBr | 100 | 96 | 2—Br—C₆H₄—CH₃ | 49 |
|  |  |  |  | 4—Br—C₆H₄—CH₃ | 50 |
| Toluene | 47% HI | 100 | 84 | 2—I—C₆H₄—CH₃ | 0 |
|  |  |  |  | 4—I—C₆H₄—CH₃ | 0 |
| Anisole | 38% HCl | 100 | 72 | 2—Cl—PhOCH₃ | 20 |
|  |  |  |  | 4—Cl—PhOCH₃ | 79 |
| Anisole | 49% HBr | 80 | 18 | 4—Br—PhOCH₃ | 99 |

The following is a proposed mechanism for the halogenation of aromatic in ionic liquids

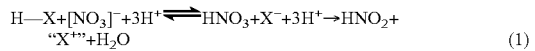

(1)

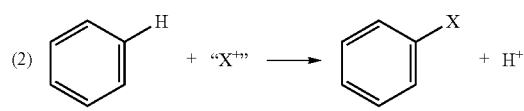

(2)

(3)

(4)

(5)

Overall 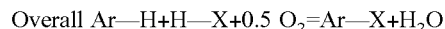
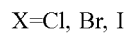

The products of these reactions can be isolated in three separate ways. Vacuum distillation allows the products to be separated from this ionic liquid, which leaves the ionic liquid dried and ready for reuse, however, this cannot be used for the separation of high molecular weight products from the ionic liquid because of the high temperatures involved. Solvent extraction with cyclohexane or diethyl ether can be used to isolate most organic products from the reaction, and the ionic liquid then regenerated by distilling off water/unreacted hydrohalic or nitric acids. The third and most successful approach is the use of steam distillation. Complete separation of the organic products from the ionic liquid can be achieved by the addition of water, followed by distillation at 120–140° C. at atmospheric pressure. The product can then be separated from the residual nitric acid usually by phase separation.

In conclusion, halogenation in ionic liquids using concentrated (68%) nitric acid and a halide salt proceeds efficiently to give the mono-halogenated product in excellent yield. The ionic liquids could all be reused in further halogenation reactions and were not destroyed, despite being in contact with acids under reflux. Separation of the products was achieved by vacuum distillation, solvent extraction, or most notably, steam distillation. The only waste from these reactions is diluted acid, which can be concentrated and recycled.

EXAMPLE

In a round-bottomed flask (25 cm³) equipped with a magnetic stirrer flea and reflux condensed, 1-butyl-3-methylimidazolium nitrate (1.00 g, 5 mmol) and toluene (0.91 g, 10 mmol) were added. 38% aqueous hydrochloric acid (2.88 g, 30 mmol) was cautiously added and the mixture heated under reflux for 96 hours. The flask was cooled and the products analysed by gas chromatography. All of the toluene had reacted and peaks due to 2- and 4-chlorotoluene (60% and 38% respectively) were observed. The products were isolated by addition of water (5 cm³) distillation at 150° C. This gave 2-phase mixture of dilute hydrochloric acid and chlorotoluene. After phase separation, the structures were confirmed by NMR analysis and were in accordance with authentic material.

The present invention also extends to the use of an ionic liquid in the halogenation of aromatic compound, as well as a halo- or polyhaloaromatic compound whenever prepared by a process of the invention.

REFERENCES

[1] De la Mare, *Electrophilic Halogenation*, Cambridge University Press, Cambridge, 1976.
[2] Nwaukwa, Keehn, *Syn. Comm.*, 1989, 19, 799.

[3] Kajigaeshi, Moriwaki, Tanaka, Fujisaki, Kakinami, Okamoto, *J. Chem. Soc., Perkin Trans.* 1, 1990, 897.
[4] Gottardi, *Monatsh. Chem.*, 1968, 99, 815.
[5] Marsh, Farnham, Sam, Smart, *J. Am. Chem. Soc.*, 1982, 104, 4680.
[6] Kovacic, Wu, Stewart, *J. Am. Chem. Soc.*, 1960, 82, 1917.
[7] Bergwerksverband G.m.b.H., British patent, GB9175721, 1960.
[8] V. A. Notaro, C. M. Selwitz, U.S. Pat. No. 3,636,170, 1972.
[9] D. I. Makhonkov, A. V. Cheprakov, M. A. Rodkin, I. P. Beletskaya, *Zhur. Org. Khim.* 1988, 24, 241–248.
[10] M. J. Earle and K. R. Seddon, *Pure and App. Chem.* 2000, in press.
[11] C. J. Adams, M. J. Earle, G. Roberts and K. R. Seddon. *Chem. Commun.* 1998, 2097–2098.
[12] C. J. Adams, M. J. Earle, J. Hamill, C. Lok, G. Roberts and K. R. Seddon, World Patent WO 98 07679, 1998.
[13] (a) B. Ellis, W. Keim and P. Wasserscheid, *Chem. Commun.* 1999, 337. (b) S. Einloft, H. Olivier and Y. Chauvin, U.S. Pat. No. 5,550,306, 1996.
[14] M. J. Earle, P. B. McCormac and K. R. Seddon, *Green Chem.* 1999, 1 23–25.
[15] (a) T. Fisher, A. Sethi, T. Welton, J. Woolf, *Tetrahedron Lett.* 1999, 40, 793–194. (b) C. J. Adams, M. J. Earle, K. R. Seddon, *Chem. Commun.* 1999, 1043–1044.
[16] T. Welton. *Chem. Rev.* 1999, 99, 2071–2083.

The invention claimed is:

1. A process for the halogenation of an aromatic compound comprising admixing the aromatic compound with a halogenating agent in the presence of an ionic liquid consisting entirely of cations and anions to form a halogenated aromatic product and water wherein the process proceeds at a temperature of −40° C. to 200° C.

2. The process as claimed in claim 1 wherein the cation of the ionic liquid is selected from the group consisting of 1-alkylpyridinium, alkylpyridium, poly-alkylpyridium, phosphonium, alkylphosphonium, polyalklphosphonium, imidazolium, alkylimidazolium, polyalkylimidazolium, ammonium, alkylammonium, polyalkylammonium, alkylpyrrazolium, polyalkylpyrrazolium, alkyloxonium, alkylsulfonium, and combinations thereof.

3. The process as claimed in claim 2 wherein the cation is 1-hexylpyridinium.

4. The process as claimed in claim 1 wherein the anion of the ionic liquid is selected from the group consisting of a halide; a nitrate; a nitrogen-containing anion other than a nitrate; an alkylsulfate; a non sulphur-containing anion based on nitrogen, phosphorus, boron, silicon, selenium, tellurium, or halogen; oxoanions of metals; anions that are based on antimony or bismuth; and combinations thereof.

5. The process as claimed in claim 4 wherein the anion is chloride, bromide, iodide or a nitrate.

6. The process as claimed in claim 1 wherein more than one ionic liquid is present.

7. The process as claimed in claim 1 wherein the ionic liquid is a water stable ionic liquid.

8. The process as claimed in claim 1 wherein the ionic liquid is selected from the group consisting of [emim]ClAlCl$_3$, [C10mim]Cl, [C$_{12}$mim]Br, [Bu$_4$N]I, 1-butyl-3-methylimidazolium nitrate, and combinations thereof.

9. The process as claimed in claim 1 wherein the halogenating agent is one or more of a nitrating agent and a hydrohalic acid.

10. The process as claimed in claim 9 wherein the nitrating agent is nitric acid.

11. The process as claimed in claim 1 wherein the halogenating agent is a halide ionic liquid.

12. The process as claimed in claim 1 wherein the reaction products are isolated by one or more of vacuum distillation, solvent extraction and steam distillation.

13. The process as claimed in claim 1 wherein the aromatic compound is benzene, toluene, biphenyl or anisole.

14. The process as claimed in claim 4 wherein the anion of the ionic liquid is methanesulfonate, trifluoromethanesulfonate or hydrogensulfate.

* * * * *